US009945789B2

(12) United States Patent
Hardcastle et al.

(10) Patent No.: US 9,945,789 B2
(45) Date of Patent: Apr. 17, 2018

(54) MULTIPLE ANALYTE DETECTION SYSTEMS AND METHODS OF DETECTING MULTIPLE ANALYTES

(75) Inventors: Ian Hardcastle, Sunnyvale, CA (US); Carol T. Schembri, San Mateo, CA (US); John Francis Petrilla, Palo Alto, CA (US); Rene B. Helbing, Palo Alto, CA (US); Daniel B. Roitman, Menlo Park, CA (US)

(73) Assignee: Alverix, Inc., Franklin Lakes, NJ (US)

( * ) Notice: Subject to any disclaimer, the term of this patent is extended or adjusted under 35 U.S.C. 154(b) by 436 days.

(21) Appl. No.: 11/653,568

(22) Filed: Jan. 16, 2007

(65) Prior Publication Data

US 2008/0171397 A1 Jul. 17, 2008

(51) Int. Cl.
*G01N 21/25* (2006.01)
*G01N 21/78* (2006.01)
(Continued)

(52) U.S. Cl.
CPC .......... *G01N 21/78* (2013.01); *G01N 21/253* (2013.01); *G01N 21/8483* (2013.01)

(58) Field of Classification Search
CPC .......... G01N 21/6428; G01N 21/6452; G01N 2021/6441; G01N 33/582; G01N 2021/7786; G01N 21/6486; G01N 2021/6439; G01N 21/8483; G01N 33/558; G01N 21/17; G01N 21/253; G01N 21/77; G01N 33/54366; G01N 33/54386; G01N 35/00732; G01N 21/78; G01N 21/76;
(Continued)

(56) References Cited

U.S. PATENT DOCUMENTS 5,478,750 A 12/1995 Bernstein et al.
5,728,587 A * 3/1998 Kang ............... G01N 33/54366
422/401
(Continued)

OTHER PUBLICATIONS

Malamud et al, Point Detection of Pathogens in Oral Samples, (2005), Departmental Papers (MEAM). 106. http://repository.upenn.edu/meam_papers/106.*
(Continued)

*Primary Examiner* — Christine T Mui
(74) *Attorney, Agent, or Firm* — Knobbe Martens Olson & Bear LLP

(57) ABSTRACT

A multiple analyte detection system includes a carrier having reagents disposed thereat, with each of the reagents capable of optically changing in response to exposure to a respective analyte. The system further includes a photodetector positioned to collectively detect light interacted with each of the reagents, a processor to determine a presence or an absence of each of the analytes in response to the light collectively-detected, and an indicator to provide an indication of the presence or the absence of each of the analytes. A method of detecting multiple analytes includes exposing reagents capable of optically changing in response to exposure to a respective analyte to a sample. The method further includes collectively detecting light interacted with each of the reagents, determining a presence or an absence of each of the analytes in response to the light collectively detected, and indicating the presence or the absence of each of the analytes determined.

26 Claims, 5 Drawing Sheets

(51) Int. Cl.
*G01N 21/84* (2006.01)
*G01N 21/17* (2006.01)

(58) Field of Classification Search
CPC ...... G01N 21/84; G01N 21/251; G01N 21/25; Y10S 436/823; A61B 2562/0295
USPC ............................ 422/52, 50; 436/164, 180
See application file for complete search history.

(56) References Cited

U.S. PATENT DOCUMENTS

| | | |
|---|---|---|
| 6,379,969 B1 | 4/2002 | Mauze et al. |
| 7,390,457 B2* | 6/2008 | Schembri ..................... 422/58 |
| 2004/0053322 A1 | 3/2004 | McDevitt et al. |
| 2004/0087033 A1* | 5/2004 | Schembri ................... 436/180 |
| 2004/0156037 A1 | 8/2004 | Mawhirt et al. |
| 2005/0019796 A1* | 1/2005 | Meiring et al. .................. 435/6 |
| 2005/0026154 A1* | 2/2005 | Bruhn et al. ..................... 435/6 |
| 2006/0142947 A1* | 6/2006 | Robrish et al. ................. 702/19 |

OTHER PUBLICATIONS

Niedbala et al, Detection of Analytes by Immunoassay Using Up-Converting Phosphor Technology, Analytical Biochemistry 293, 2001, 22-30.*

Abdul-Ahad W et al., Immunoassays—A Practical Approach: Chapter 4—Labels and endpoints (2000), Gosling J. P. [Ed.]; Oxford University Press, pp. 89-97.

Ullman E.F., The Immunoassay Handbook: Chapter 12—Homogeneous Immunoassays; 3rd Edition, (2005), David Wild [Ed.], Elsevier Ltd., pp. 212-232.

Wild D. et al., The Immunoassay Handbook: Chapter 2—Components, (1994), David Wild [Ed.], Stockton Press, pp. 62-82.

* cited by examiner

MULTIPLE ANALYTE DETECTION SYSTEMS AND METHODS OF DETECTING MULTIPLE ANALYTES

BACKGROUND

Analytical chemistry has been instrumental in providing healthier and more comfortable living for billions of people around the world. For example, samples of water, air, microorganisms, and tissues from plants and animals are analyzed for environmental protection purposes. In the medical field, samples of body tissues and physiological fluids are analyzed to provide information on patients, e.g., for diagnosis and for monitoring purposes. In the past, analyses were mostly done by collecting samples and bringing them to a laboratory for analysis by large, relatively expensive and complex pieces of equipment.

As an alternative to laboratory analysis, disposable test strips, e.g., lateral flow devices, similar to those used in home pregnancy tests, are employed in testing in the field, e.g., point-of-care testing. Test strips for detecting multiple analytes generally include multiple reagents located on a carrier member, in which each reagent changes color in the presence or absence of a particular analyte. The change in color provides a visual qualitative indication to a user as to whether or not the respective analyte is present in the sample. However, oftentimes it is difficult for the user to determine whether or not a color change has actually occurred. As a result, the user frequently has to redo the test, which can be frustrating.

Accordingly, a continuing need exists for improved devices and methods for detecting multiple analytes that are both easy to use and accurate, while also allowing for testing in the field, e.g., point-of-care testing.

SUMMARY

A multiple analyte detection system of the present invention is presented. The system includes a carrier having reagents disposed thereat. Each of the reagents is capable of optically changing in response to exposure to a respective analyte. The system also includes a photodetector positioned to collectively detect light interacted with each of the reagents. The photodetector provides a signal indicative of the light detected. The system further includes a processor to process the signal from the photodetector to determine a presence or an absence of each of the analytes and an indicator in communication with the processor to provide an indication of the presence or the absence of each of the analytes.

A method of detecting multiple analytes of the present invention is also presented. The method includes exposing reagents to a sample. Each of the reagents is capable of optically changing in response to exposure to a respective analyte. The method also includes collectively detecting light interacted with each of the reagents. The method further includes determining a presence or an absence of each of the analytes in response to the light collectively detected and indicating the presence or the absence of each of the analytes determined.

A reader for a test strip supporting multiple reagents of the present invention is also presented. Each of the reagents is capable of optically changing in response to exposure to a reactive analyte. The reader includes a photodetector to collectively detect light interacted with each of the reagents. The photodetector provides a signal indicative of the light detected. The reader further includes a processor to process the signal from the photodetector to determine a presence or an absence of each of the reactive analytes and an indicator in communication with the processor to provide an indication of the presence or the absence of each of the reactive analytes.

The above-described and other features will be appreciated and understood from the following detailed description, drawings, and appended claims.

BRIEF DESCRIPTION OF THE DRAWINGS

Referring now to the figures, which are exemplary embodiments, and in which the like elements are numbered alike.

DETAILED DESCRIPTION

Figure 1:
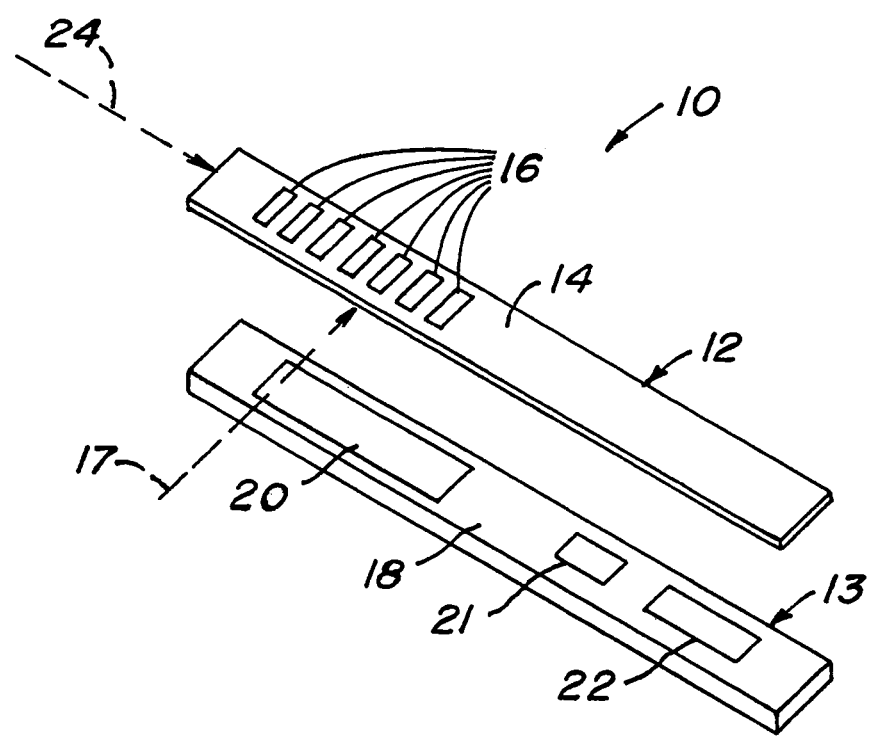
FIG. 1 is an exploded perspective view of a multiple analyte detection system in accordance with an embodiment of the present invention.

Referring to FIG. 1, a multiple analyte detection system in accordance with an embodiment of the present invention is generally shown at 10. System 10 includes a test strip 12 and a reader 13. Test strip 12 comprises a carrier 14 supporting reagents 16. The reagents can be adhered to the carrier 14, absorbed into the carrier 14, or deposited on the carrier 14 in any suitable manner, many of which are known. Reagents 16 include any substance that interacts with an analyte in a sample to which test strip 12 is exposed to optically change in the presence or absence of the analyte. Examples of such substances include chemical reagents (e.g., organic or inorganic compounds), biological reagents (e.g., antibodies), and elements (e.g., gold particles). One of the reagents 16 optically changes when it comes into contact with the sample; in other words, this reagent is a sample detection reagent.

The reagents 16 in the present embodiment are longitudinally displaced and have mutually different reaction times with their respective analytes. The reagents are simultaneously exposed to a lateral flow of the sample, i.e., a flow across test strip 12 in the direction indicated by an arrow 17 in this embodiment. When simultaneously exposed to a sample in which the respective analytes are present or absent, the reagents optically change sequentially, as will be described in more detail below.

The carrier 14 is composed of a transparent material, e.g., glass or plastic, to facilitate transfer of light passing through the reagents 16.

The reader 13 comprises a housing 18 supporting a photodetector 20 and a signal processor 21, which are electronically connected. Housing 18 is configured to support or receive test strip 12 with reagents 16 being positioned directly over photodetector 20 such that light passing through each of the reagents 16 and carrier 14 is collectively detected by photodetector 20. This mode of operation is referred to throughout this disclosure as the transmittance mode. In the transmittance mode, the amount of light absorbed by each reagent 16 changes in the presence or absence of the respective analyte. The remaining light, e.g., the un-absorbed light, is transmitted and is detected by photodetector 20.

An indicator 22 is also supported by housing 18 and is electrically connected to processor 21. In an embodiment, indicator 22 includes the ability to process signals, such that the processor 21 is integrated into the indicator 22. Indicator 22 is positioned to be visible through the transparent carrier 14. Indicator 22 indicates the presence of the analytes by a positive indication when present. Alternatively, indicator 22 indicates the concentration of each of the analytes in the sample. The concentration is expressed in absolute units or expressed on an arbitrary scale; for example, an indicator employing an arbitrary scale of 1 to 5, where 1 is indicative of a lower concentration than 5 and each step on the scale corresponds to a discrete analyte concentration range. Indicator 22 comprises any suitable visual indicator, such as a liquid crystal display (LCD) or a light source such as a light emitting diode (LED). Alternatively, indicator 22 comprises an indicator for each of the analytes, e.g., each indicating when the respective analyte is detected. In another embodiment, indicator 22 comprises an audio indicator, such as a horn, a buzzer, or a beeper.

Processor 21 receives from photodetector 20 a signal resulting from an optical change of the sample detection reagent and compares the signal to a threshold value to determine the presence of the sample. Once the processor 21 has determined that a sample has been detected the processor 21 then compares the temporal variation of the signal received from photodetector 20 to a set of templates (not shown) stored in the processor. Each template represents a temporal variation of the photodetector signal expected to occur as a result of the presence or absence of a different combination of analytes in a sample. Processor 21 performs the comparison to identify the template that most closely matches the temporal variation of the photodetector signal. Processor 21 then provides to indicator 22 a signal that causes the indicator 22 to indicate the presence or absence of the analytes corresponding to the presence or absence of analytes indicated by the identified template.

In an alternative embodiment, processor 21 receives from photodetector 20 a signal resulting from an optical change of the sample detection reagent and compares the signal to a threshold value to determine the presence of the sample. Once the processor 21 has determined that a sample has been detected the processor 21 then compares changes in the signal from the photodetector 20 to a threshold value to detect discrete changes within defined time intervals. These time intervals correspond with time intervals of expected reactions of each of the reagents. A discrete change within a time interval will indicate the presence of a respective analyte, while no change during that time interval will indicate the absence of the respective analyte. Processor 21 then provides an appropriate signal to indicator 22 to indicate the presence or concentration of the analytes, as described above.

In an embodiment, the processor 21 digitally processes the signal generated by the photodetector 20. In this case the processor 21 is a microprocessor, and photodetector 20 or processor 21 includes an analog-to-digital (A-D) converter (not shown). Alternatively, processor 21 is a programmable logic device (PLD), an application-specific integrated circuit (ASIC) or any other suitable device for digitally comparing the signal.

A battery (not shown) is disposed in housing 18 and is electrically connected to photodetector 20, processor 21, and indicator 22 to provide power thereto.

Except for the sample detection reagent, which optically changes when it comes into contact with the sample, the reagents 16 optically change in response to the presence or absence of a particular analyte in a sample to which the test strip 12 is exposed. For example, the absorption of light at a selected wavelength changes. A reagent 16 that changes optically in the presence of the particular analyte is referred to as a positive-type test. A reagent that changes optically in the absence of the particular analyte is referred to as a negative-type test. Both positive-type and negative-type test are contemplated by the present invention. Also, a reagent may be selected that does not change optically in the presence of the particular analyte for a positive-type test or the absence of a particular analyte for a negative-type test. When no optical change is indicative of the presence of the particular analyte for a positive-type test or the absence of the particular analyte for a negative-type test, such is considered an optical change.

The reagents 16 may each be unique to a particular analyte, or two or more of the reagents may be directed to the same analyte, such being dictated by a particular application of the test strip 12. Moreover, the reagents 16 have mutually different reaction rates. For example, each reagent 16 changes optically at a different time after exposure to the sample. The length of time for each of the reagents 16 to change optically is long enough that photodetector 20 can detect that optical change before another one of the reagents 16 changes optically. With each of the reagents reacting at a different time, a sample can flow laterally across test strip 12, as indicated by arrow 17, reacting with the reagents 16 simultaneously, while single photodetector 20 detects each optical change individually, as the changes occur at different times. The sample detection reagent optically changes upon contact with the sample, i.e., without any temporal displacement.

In an alternative embodiment, the reagents 16 do not have mutually different reaction rates. They have the same or similar reaction rates. The sample flow is longitudinal relative to test strip 12, as indicated by an arrow 24. This allows the sample to react with each of the reagents sequentially, and results in sequential optical changes. For example, the sample flows from one reagent 16 to the next reagent 16, e.g., by capillary action, and the sample does not react with multiple reagents 16 simultaneously. The distance between adjacent reagents 16 in the longitudinal direction is selected to achieve desired time intervals between reactions of the sample with the reagents 16 and desired time intervals in the optical changes resulting from the reactions. Also, one or both of the material composition and surface features, e.g., pore size, of carrier 14, at least in the area of the reagents 16, is selected to achieve a desired flow rate of the sample. As in the lateral flow embodiment, single photodetector 20 detects each optical change individually, as the optical changes each occur at different times. In this embodiment, the sample detection reagent is disposed towards the end of the test strip 12 to be the first of the reagents to come into contact with the sample.

Any configuration of the reagents 16 that provides for temporally-sequential optical changes resulting from the reaction of the sample with the reagents 16, which permits use of a single photodetector 20 to detect these optical changes, is within the scope of the present invention. Photodetector 20 comprises any suitable single photodetector capable of detecting the optical changes. Examples include a solid-state diode and a CMOS (Complementary Metal Oxide Semiconductor) detector.

Figure 2:
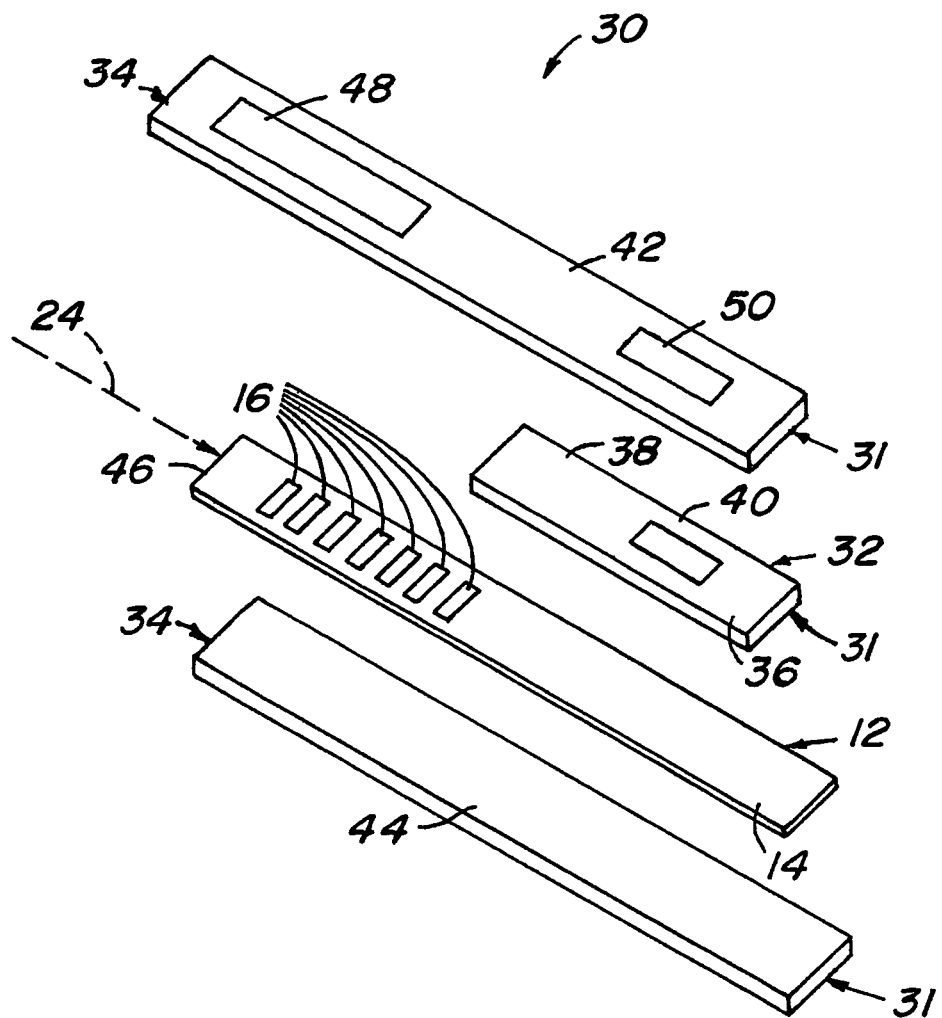
FIG. 2 is an exploded perspective view of a multiple analyte detection system in accordance another embodiment of the present invention.

Referring to FIG. 2, a multiple analyte detection system in accordance with another embodiment of the present invention is generally shown at 30. System 30 includes test strip 12 and a reader 31. Reader 31 includes a photodetector module 32 supported by a housing 34. Cooperating housing portions 42 and 44 form housing 34. Test strip 12 is the same as described above with reference to FIG. 1. Housing 34 is configured to support or receive test strip 12 with one end 46 of test strip 12 extending beyond the housing 34 to allow test strip 12 to contact a sample. Photodetector module 32 comprises a base 36 supporting a photodetector 38 and a signal processor 40, which are electrically connected. Housing portion 42 defines a transparent window 48 positioned directly above the reagents 16 such that light passing through window 48 illuminates the reagents 16.

Light returned by each of the reagents 16 is collectively detected by photodetector 38, which is longitudinally displaced from reagents 16. Light is typically returned by reflection, scattering or a combination of reflection or scattering. For simplicity, this mode of operation will be referred to throughout this disclosure as the reflectance mode. In the reflectance mode, the amount of light absorbed by each reagent 16 changes in the presence or absence of the respective analyte. The remaining light, i.e., the un-absorbed light, is returned towards photodetector 38, where it is detected. Photodetector 38 comprises any suitable single photodetector capable of detecting the optical changes. Examples include a solid-state diode and a CMOS (Complementary Metal Oxide Semiconductor) detector.

An indicator 50 is also supported at housing portion 42 and is electrically connected to processor 40. In an embodiment, indicator 50 includes the ability to process signals, such that the processor 40 is integrated into the indicator 50. Indicator 50 indicates the presence of each of the analytes by a respective positive indication when present. Alternatively, indicator 50 indicates the concentration of each of the analytes in the sample. The concentration is expressed in absolute units or expressed on an arbitrary scale; for example, an indicator employing an arbitrary scale of 1 to 5, where 1 is indicative of a lower concentration than 5 and each step on the scale corresponds to a discrete analyte concentration range. Indicator 50 comprises any suitable visual indicator, such as a liquid crystal display (LCD) or a light source such as a light emitting diode (LED). Alternatively, indicator 50 comprises an indicator for each of the analytes, e.g., each indicating when the respective analyte is detected. In another embodiment, indicator 50 comprises an audio indicator, such as a horn, a buzzer, or a beeper.

Processor 40 receives from photodetector 38 a signal resulting from an optical change of the sample detection reagent and compares the signal to a threshold value to determine the presence of the sample. Once the processor 40 has determined that a sample has been detected the processor 40 then compares the temporal variation of the signal received from photodetector 38 to a set of templates (not shown) stored in the processor. Each template represents a temporal variation of the photodetector signal expected to occur as a result of the presence or absence of a different combination of analytes in a sample. Processor 40 performs the comparison to identify the template that most closely matches the temporal variation of the photodetector signal. Processor 40 then provides to indicator 50 a signal that causes the indicator 50 to indicate the presence or absence of the analytes corresponding to the presence or absence of analytes indicated by the identified template.

In an alternative embodiment, processor 40 receives from photodetector 38 a signal resulting from an optical change of the sample detection reagent and compares the signal to a threshold value to determine the presence of the sample. Once the processor 40 has determined that a sample has been detected, the processor 40 then compares changes in the signal from the photodetector 38 to a threshold value to detect discrete changes within defined time intervals. These time intervals correspond with time intervals of expected reactions of each of the reagents. A discrete change within a time interval will indicate the presence of a respective analyte, while no change during that time interval will indicate the absence of the respective analyte. Processor 40 then provides an appropriate signal to indicator 50 to indicate the presence or concentration of the analytes, as described above.

In an embodiment, the processor 40 digitally processes the signal generated by the photodetector 38. In this case the processor 40 is a microprocessor, and photodetector 38 or processor 40 includes an analog-to-digital (A-D) converter (not shown). Alternatively, processor 40 is a programmable logic device (PLD), an application-specific integrated circuit (ASIC) or any other suitable device for digitally comparing the signal.

A battery (not shown) is disposed in housing 34 and is electrically connected to photodetector 38, processor 40, and indicator 50 to provide power thereto.

The sample is applied to test strip 12 at the end 46 thereof, such that the sample propagates longitudinally down the test strip to the reagents. In this embodiment, the reagents 16 have the same or similar reaction rates. The sample flow is longitudinal relative to test strip 12, as indicated by an arrow 24, allowing the sample to react with the reagents sequentially, resulting in sequential optical changes. The flow rate of the sample is controlled and the spacing of the reagents 16 along the test strip 12 is selected to accomplish the desired temporal sequence of the optical changes of the reagents 16, as discussed above with reference to the embodiment shown in FIG. 1. The sample detection reagent is disposed towards the end 46 of the test strip 12 to be the first of the reagents to come into contact with the sample.

In an alternative embodiment, window 48 provides an opening through which the sample is deposited directly on the reagents 16. In this case, the end 46 of test strip 12 does not need to extend beyond housing 34. The reagents 16 have mutually different reaction rates. The length of time for each of the reagents to change optically is long enough that photodetector 38 can detect that optical change before another one of the reagents 16 changes optically. With each of the reagents 16 reacting at a different time, the sample can react with the reagents 16 simultaneously.

As in the embodiment of FIG. 1, in the embodiment of FIG. 2, any configuration of the reagents 16 that provides for temporally-sequential optical changes resulting from the reaction of the sample with the reagents 16, which permits use of a single photodetector 38 to detect these optical changes, is within the scope of the present invention.

Figure 3:
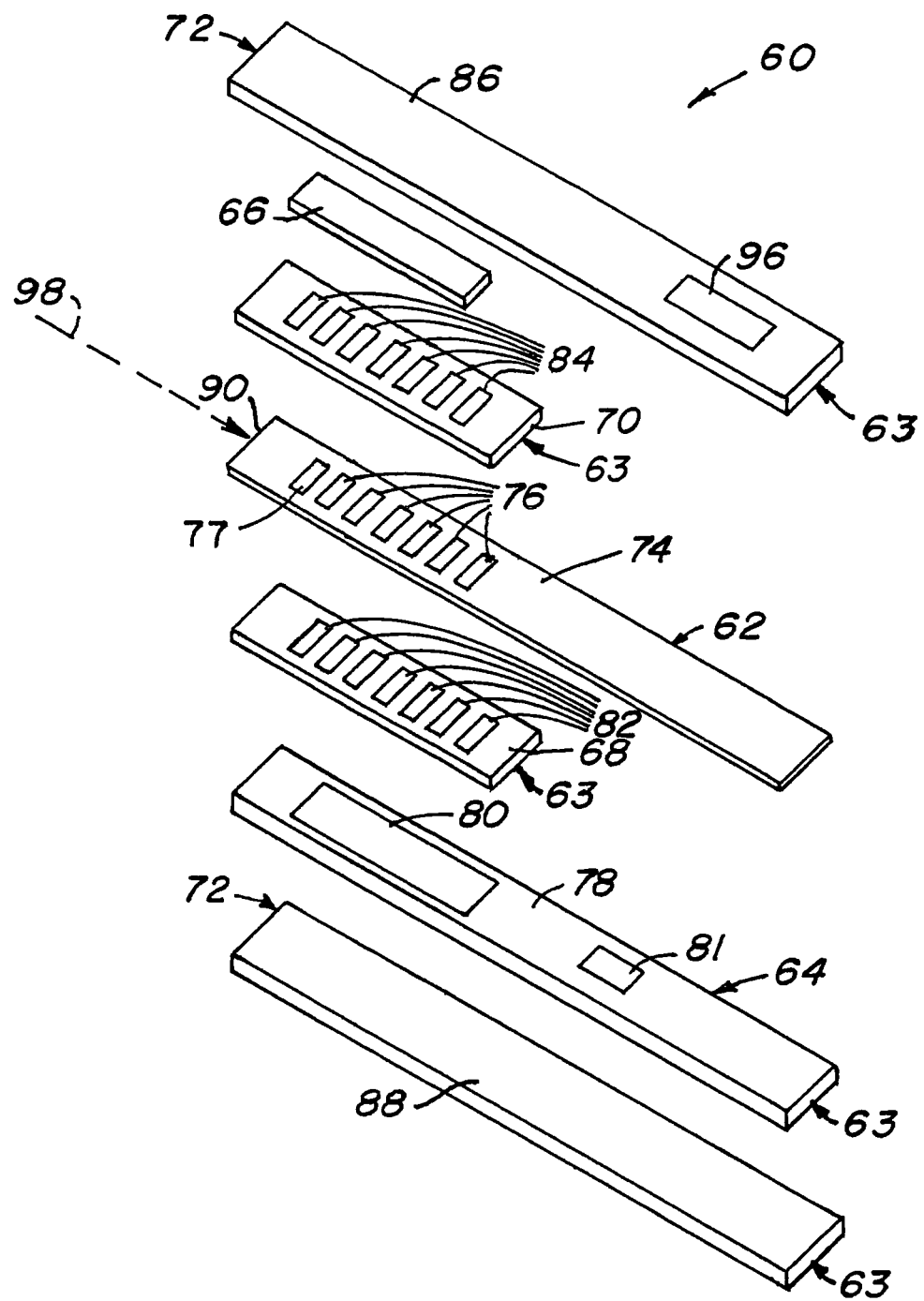
FIG. 3 is an exploded view of a multiple analyte detection system in accordance with yet another embodiment of the present invention.

Referring to FIG. 3, a multiple analyte detection system in accordance with still another embodiment of the present invention is generally shown at 60. System 60 includes a test strip 62 and a reader 63. Reader 63 includes a photodetector module 64, a light source 66, an optical filter 68, and a baffle 70, supported by a housing 72. Cooperating housing portions 86 and 88 form housing 72. Housing 72 is configured to support or receive test strip 62 with one end 90 of test strip 62 extending beyond the housing 72 to allow test strip 62 to contact the sample. Test strip 62 comprises a carrier 74 supporting reagents 76. Reagents 76 are the same as reagents 16 discussed above with reference to the embodiments shown in FIGS. 1 and 2. The reagents can be adhered to the carrier 74, absorbed into the carrier 74, or deposited on the carrier 74 in any suitable manner, many of which are known. The reagents in the present embodiment are longitudinally displaced. One of the reagents designated 77 is neutral or essentially lacking a reagent, in that it does not react to any of the analytes. Reagent 77 is used to provide a control baseline for comparing the optical changes for the various reagents. In other words, this is a way of determining if anything, e.g., a pigment or colorant in the sample, other than the analytes causes an optical change. The carrier 74 is composed of a transparent material, e.g., glass or plastic, to facilitate transfer of light passing through the reagents 76, 77.

The photodetector module 64 comprises a base 78 supporting a photodetector 80 and a signal processor 81, which are electrically connected. Base 78 is additionally configured to support test strip 62 with reagents 76, 77 being positioned directly over photodetector 80, such that light passing through the reagents 76, 77 and carrier 74 is detected by photodetector 80. System 60 operates in the transmittance mode, as described above. In the transmittance mode, the amount of light absorbed by each reagent 76 changes in the presence or absence of the respective analyte. The remaining light, i.e., the un-absorbed light is transmitted and is collectively detected by photodetector 80. Photodetector 80 comprises any suitable single photodetector capable of detecting the optical changes. Examples include a solid-state diode and a CMOS (Complementary Metal Oxide Semiconductor) detector.

Optical filter 68 includes optical filters 82 corresponding in size, shape, and location to the reagents 76, 77. Optical filter 68 optically filters the light passing from the reagents 76, 77 to photodetector 80. Optical filter 68 is comprised of a suitable material, such as, plastic, glass, quartz, silicon dioxide, and silicon nitride. Each optical filter 82 transmits light in a range of frequencies corresponding to the range of frequencies absorbed by the respective reagent 76. Alternatively, optical filter 68 is configured as a single optical filter that transmits light in a range of frequencies corresponding to the frequencies collectively absorbed by the reagents 76. Optical filter 68 results in more accurate detection of the optical changes, as it prevents photodetector 80 from being exposed to light outside the frequency range of interest.

Baffle 70 includes openings 84 corresponding in size, shape, and location with the reagents 76, 77. Baffle 70 directs light from light source 66 to the reagents. Baffle 70 is formed of an opaque material. Light source 66 emits light at a single frequency, in a narrow spectrum or in a broad spectrum and is composed of one or more light emitting diodes (LEDs) or edge-emitting or surface-emitting laser diodes.

An indicator 96 is also supported at housing portion 86 and is electrically connected to processor 81. In an embodiment, indicator 96 includes the ability to process signals, such that the processor 81 is integrated into the indicator 96. Indicator 96 indicates the presence of each of the analytes by a respective positive indication when present. Alternatively, indicator 96 indicates the concentration of each of the analytes in the sample. The concentration is expressed in absolute units or expressed on an arbitrary scale; for example, an indicator employing an arbitrary scale of 1 to 5, where 1 is indicative of a lower concentration than 5 and each step on the scale corresponds to a discrete analyte concentration range. Indicator 96 comprises any suitable visual indicator, such as a liquid crystal display (LCD) or a light source such as a light emitting diode (LED). Alternatively, indicator 96 comprises an indicator for each of the analytes, e.g., each indicating when the respective analyte is detected. In another embodiment, indicator 96 comprises an audio indicator, such as a horn, a buzzer, or a beeper.

Processor 81 receives from photodetector 80 a signal resulting from an optical change of the sample detection reagent and compares the signal to a threshold value to determine the presence of the sample. Once the processor 81 has determined that a sample has been detected the processor 81 then compares the temporal variation of the signal received from photodetector 80 to a set of templates (not shown) stored in the processor. Each template represents a temporal variation of the photodetector signal expected to occur as a result of the presence or absence of a different combination of analytes in a sample. Processor 81 performs the comparison to identify the template that most closely matches the temporal variation of the photodetector signal. Processor 81 then provides to indicator 96 a signal that causes the indicator 96 to indicate the presence or absence of the analytes corresponding to the presence or absence of analytes indicated by the identified template.

In an alternative embodiment, processor 81 receives from photodetector 80 a signal resulting from an optical change of the sample detection reagent and compares the signal to a threshold value to determine the presence of the sample. Once the processor 81 has determined that a sample has been detected, the processor 81 then compares changes in the signal from the photodetector 80 to a threshold value to detect discrete changes within defined time intervals. These time intervals correspond with time intervals of expected reactions of each of the reagents. A discrete change within a time interval will indicate the presence of a respective analyte, while no change during that time interval will indicate the absence of the respective analyte. Processor 81 then provides an appropriate signal to indicator 96 to indicate the presence or concentration of the analytes, as described above.

In an embodiment, the processor 81 digitally processes the signal generated by the photodetector 80. In this case the processor 81 is a microprocessor, and photodetector 80 or processor 81 includes an analog-to-digital (A-D) converter (not shown). Alternatively, processor 81 is a programmable logic device (PLD), an application-specific integrated circuit (ASIC) or any other suitable device for digitally comparing the signal.

A battery (not shown) is disposed in housing 72 and is electrically connected to photodetector 80, processor 81, light source 66, and indicator 96 to provide power thereto.

The sample is applied to test strip 62 at the end 90 thereof, such that the sample propagates longitudinally down the test strip to the reagents. In this embodiment, the reagents 76 have the same or similar reaction rates. The sample flow is longitudinal relative to test strip 62, as indicated by an arrow 98, allowing the sample to react with the reagents sequentially, resulting in sequential optical changes. The flow rate of the sample is controlled and the spacing of the reagents along the test strip is selected to accomplish the desired temporal sequence of the optical changes of the reagents, as discussed above with reference to the embodiment shown in FIG. 1.

As in the embodiments of FIGS. 1 and 2, in the embodiment of FIG. 3, any configuration of the reagents 76 that provides for temporally-sequential optical changes resulting from the reaction of the sample with the reagents, which permits use of a single photodetector 80 to detect these optical changes, is within the scope of the present invention.

Figure 4:
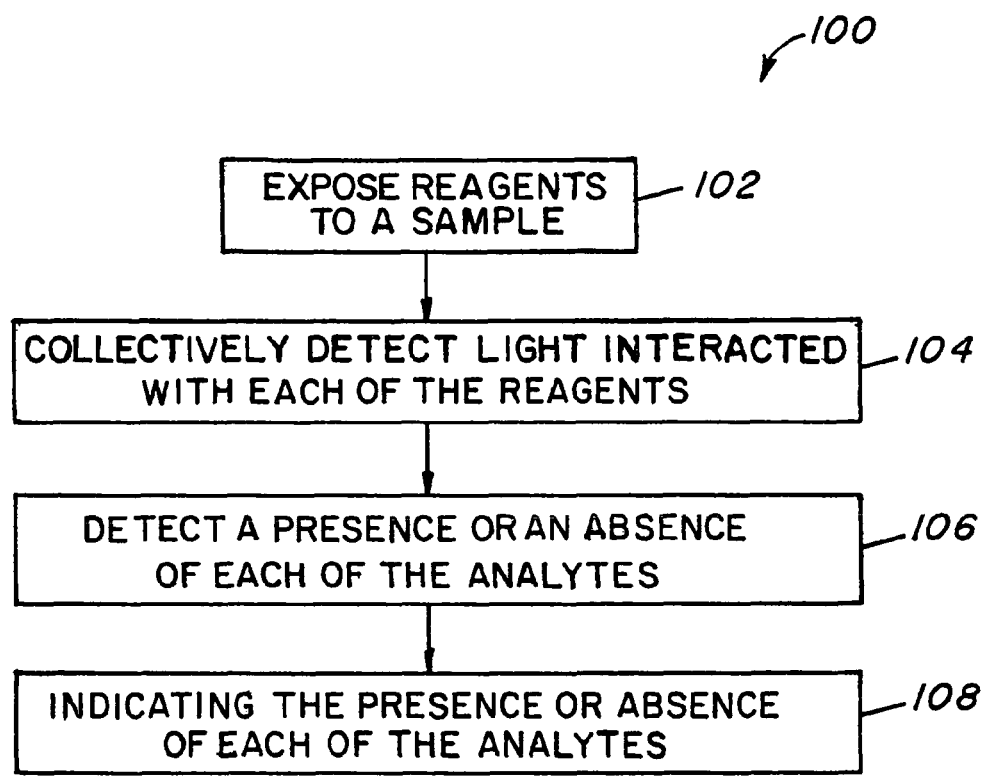
FIG. 4 is a flow chart illustrating a method of detecting multiple analytes in accordance with an embodiment of the present invention.

Referring now to FIG. 4, a method of detecting multiple analytes in accordance with an embodiment of the present invention is generally shown at 100. Reagents are exposed to a sample, as indicated by block 102. The reagents are the same as the reagents 16, 76 discussed above with reference to the embodiments shown in FIGS. 1-3. The sample is exposed to the reagents by a lateral or a longitudinal flow of the sample. Light interacted with each of the reagents is collectively detected, as indicated by block 104. The optical changes of the reagents are measured collectively, but not at the same time since the reactions are temporally displaced. A presence or an absence of each of the analytes is detected in response to the light collectively detected, as indicated at block 106. Finally, the presence or the absence of each of the analytes determined is indicated, as indicated by block 108.

Figure 5:
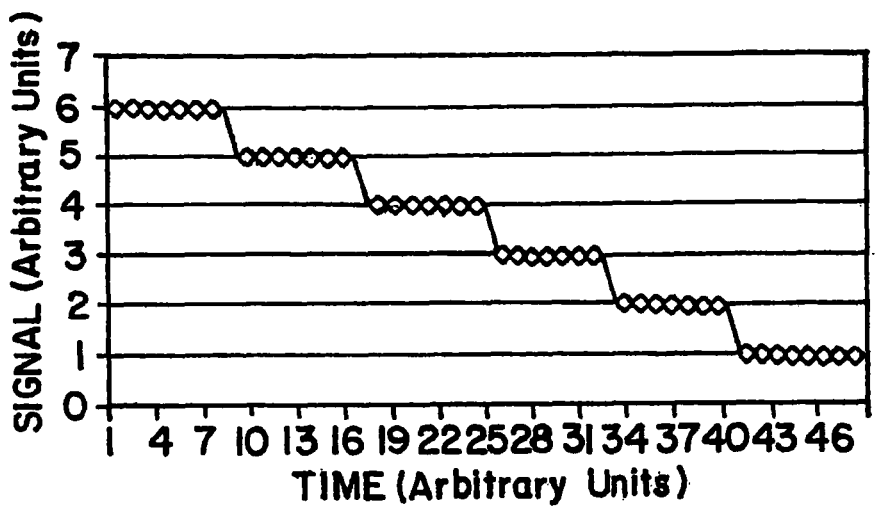
FIG. 5 is a graph of signal output as a function of time in an example in which six reagents exposed to all of the expected analytes.

FIG. 5 graphically illustrates the variation as a function of time of the signal output from the single photodetector, i.e., any one of the single photodetectors in the embodiments shown in FIGS. 1-3, in an example in which six reagents are exposed to a sample in which all the analytes are present. The signal resulting from the seventh reagent, i.e., the sample detection reagent is not shown. Signal output and time are both expressed in arbitrary units. The presence of each respective analyte is graphically illustrated as a step function; that is, the signal level decreases incrementally each time another analyte is detected. In this example, the reagents have the same reaction rate, and the flow rate of the sample is longitudinal and constant down the test strip. The same results would have been achieved with a lateral flow of the sample or simultaneous exposure to the sample, with the reagents having mutually different reaction times.

Figure 6:
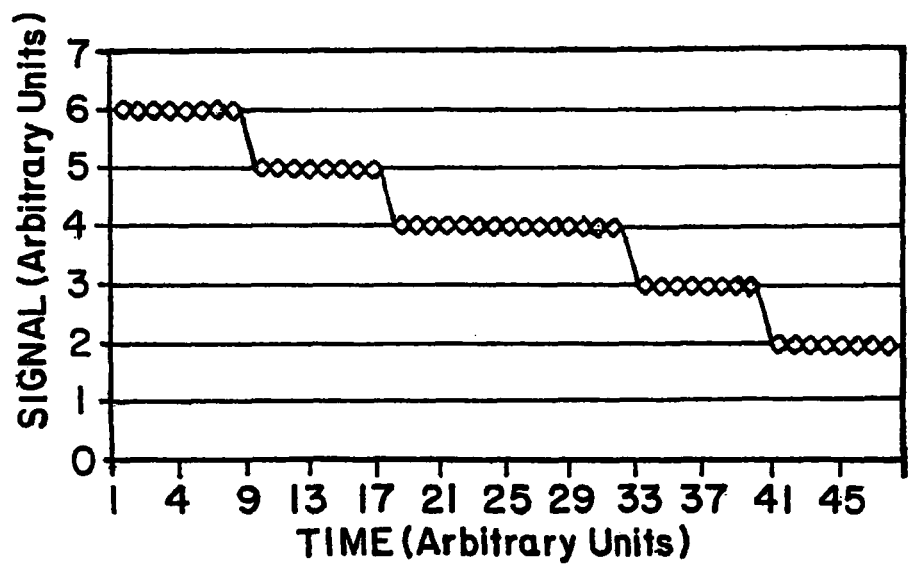
FIG. 6 is a graph of signal output as a function of time in an example in which six reagents exposed to all but one of the expected analytes.

FIG. 6 graphically illustrates the variation as a function of time of the signal output from the single photodetector, i.e., any one of the single photodetectors in the embodiments shown in FIGS. 1-3, in an example in which six reagents are exposed to a sample in which all but one of the analytes is present. The signal resulting from the seventh reagent, i.e., the sample detection reagent is not shown. Signal output and time are both expressed in arbitrary units. The presence of each respective analyte is graphically illustrated as a step function; that is, the signal level decreases incrementally each time another analyte is detected. The omitted analyte is the fourth analyte, such that there is no change during the time in which the fourth analyte would be detected. In this example, the reagents all have the same reaction rate, and the flow rate of the sample is longitudinal and constant down the test strip. The same results would have been achieved with a lateral flow of the sample or simultaneous exposure to the sample, with the reagents having mutually different reaction times.

Advantageously, the multiple analyte detection systems and methods are suited for any field where a sample possibly comprising multiple analytes is to be analyzed. For example, these multiple analyte detection systems and methods can be employed in forensic science, environmental science, medical science, and geology. Further, the multiple analyte detection systems and methods can be employed with existing test strip technology. The multiple analyte detection systems can be employed for in-the-field testing, e.g., point-of-care type testing, which advantageously allows diagnostic tests to be provided to individuals that may otherwise not have access to this type of multiple analyte detection. For example, multiple analyte detection systems configured for medial applications can be readily employed without any regard to geographic location, e.g., in third world countries.

The use of a single photodetector advantageously provides single-use multiple analyte detection devices to be produced that allow multiple analytes to be quantitatively analyzed. As such, the single-use multiple analyte detection devices can quantitatively detect multiple analytes in a sample at a lower cost than, for example, systems where multiple photodetectors are employed or systems configured to analyze a single analyte. Advantageously, the single photodetector detects the presence or absence of multiple analytes without having to move either the photodetector and/or the reagents during the measuring process.

This disclosure describes the invention in detail using illustrative embodiments. Various changes may be made and equivalents may be substituted without departing from the scope of the invention. The invention defined by the appended claims is not limited to the precise embodiments disclosed.

We claim:

1. A multiple analyte detection system configured to detect the presence or absence of multiple analytes in a single sample during a diagnostic test, comprising:
   a test strip comprising
     a plurality of reagents, each reagent changing optically after exposure to a particular analyte, wherein the rate of reaction of each reagent after exposure to its particular analyte is different than the rate of reaction of each other reagent after exposure to its respective analyte, such that, after simultaneous exposure to a combination of analytes in the single sample, optical change of each reagent after exposure to its particular analyte starts at a different time than optical change of each other reagent after exposure to its respective analyte, and
     a carrier having the plurality of reagents physically displaced relative to each other along a longitudinal axis of the carrier, the carrier configured to flow the single sample laterally across the carrier in a direction generally perpendicular to the longitudinal axis of the carrier and expose the plurality of reagents simultaneously to the combination of analytes, wherein optical change of each reagent after exposure to its particular analyte occurs during a defined time interval of a plurality of sequential time intervals during a measuring process of the diagnostic test;
   a single photodetector that generates, following simultaneous exposure of the plurality of reagents to the combination of analytes in the single sample, a temporally varied signal as each of the reagents optically changes sequentially in response to exposure to its respective analyte, wherein the time interval during which each of the reagents changes optically is long enough that the single photodetector iteratively detects, during the measuring process, the optical change of each of the reagents before another one of the reagents changes optically;
   a processor programmed to compare the temporally varied signal received from the single photodetector to a set of temporally varied templates stored in the processor to identify a temporally varied template that matches the temporally varied signal, wherein each temporally varied template in the set represents a temporally varied signal expected to occur as a result of the presence or absence of a different combination of analytes in a test sample; and an indicator in communication with the processor for providing an indication of the presence or the absence of each of the analytes in the combination of analytes in the single sample applied to the test strip.

2. The multiple analyte detection system of claim 1, wherein the photodetector is positioned to collectively detect light transmitted through each of the reagents.

3. The multiple analyte detection system of claim 1, wherein the photodetector is positioned to collectively detect light returned by each of the reagents.

4. The multiple analyte detection system of claim 1, further comprising: a light source positioned to provide light for interacting with the reagents.

5. The multiple analyte detection system of claim 1, wherein the processor is integral to one of the photodetector and the indicator.

6. The multiple analyte detection system of claim 1, wherein the carrier further comprises a sample detection reagent that optically changes when it comes into contact with the single sample.

7. The multiple analyte detection system of claim 6, wherein the photodetector is positioned to detect light interacted with the sample detection reagent and generate a signal, and wherein the processor compares the signal from the photodetector to a threshold value to determine the presence of the sample.

8. The multiple analyte detection system of claim 1, further comprising: a filter positioned to filter light interacted with each of the reagents.

9. A method of detecting multiple analytes, comprising:
exposing reagents to a sample, each of the reagents capable of optically changing in response to exposure to a respective analyte;
collectively detecting light interacted with each of the reagents;
determining a presence or an absence of each of the analytes in response to the light collectively detected; and
indicating the presence or the absence of each of the analytes determined.

10. The method of detecting multiple analytes of claim 9, wherein the reagents optically change at mutually different times.

11. The method of detecting multiple analytes of claim 10, wherein the reagents have mutually different reaction times, and the exposing comprises: substantially simultaneously exposing the reagents to the sample.

12. The method of detecting multiple analytes of claim 9, wherein the detecting comprises: collectively detecting light transmitted through each of the reagents.

13. The method of detecting multiple analytes of claim 9, wherein the detecting comprises: collectively detecting light returned by each of the reagents.

14. The method of detecting multiple analytes of claim 9, wherein the determining comprises: processing information indicative of the light collectively detected to determine the presence or the absence of each of the analytes.

15. The method of detecting multiple analytes of claim 9, wherein the determining comprises: comparing temporal variation of the light collectively detected to determine the presence or the absence of each of the analytes.

16. The method of detecting multiple analytes of claim 9, wherein the determining comprises: detecting discrete changes of the light collectively detected within defined time intervals to determine the presence or the absence of each of the analytes.

17. A system for reading a test strip, comprising:
a plurality of reagents, each reagent changing optically after exposure to a particular analyte, wherein the rate of reaction of each reagent after exposure to its particular analyte is different than the rate of reaction of each other reagent after exposure to its respective analyte, such that, after simultaneous exposure to a combination of analytes in a single sample, optical change of each reagent after exposure to its particular analyte starts at a different time than optical change of each other reagent after exposure to its respective analyte;
a test strip supporting the plurality of reagents arranged along a longitudinal axis of the test strip, the test strip configured to flow the single sample across the test strip such that the plurality of reagents are simultaneously exposed to the combination of analytes upon application of the single sample to the test strip, wherein optical change of each reagent after exposure to its particular analyte occurs during a defined time interval of a plurality of sequential time intervals during a measuring process;
a single photodetector that generates a temporally varied signal as each of the reagents optically changes sequentially following simultaneous exposure to the combination of analytes in the single sample, wherein the time interval during which each of the reagents changes optically is long enough that the single photodetector iteratively detects, during the measuring process, the optical change of each of the reagents before another one of the reagents changes optically;
a processor programmed to compare the temporally varied signal received from the single photodetector to a set of temporally varied templates stored in the processor to identify a temporally varied template that matches the temporally varied signal, wherein each temporally varied template in the set represents a temporally varied signal expected to occur as a result of the presence or absence of a different combination of analytes in a test sample; and
an indicator in communication with the processor for providing an indication of the presence or the absence of each of the reactive analytes in the combination of analytes in the single sample applied to the test strip.

18. The system of claim 17, wherein the photodetector is positioned to collectively detect light transmitted through each of the reagents.

19. The system of claim 17, wherein the photodetector is positioned to collectively detect light returned by each of the reagents.

20. The system of claim 17, further comprising: a light source positioned to provide light for interacting with the reagents.

21. The system of claim 17, wherein the processor is integral to one of the photodetector and the indicator.

22. The system of claim 17, further comprising: a filter positioned to filter light interacted with each of the reagents.

23. The multiple analyte detection system of claim 1, wherein the single photodetector is stationary relative to the carrier during the measuring process.

24. The multiple analyte detection system of claim 1, wherein the plurality of reagents includes N reagents, wherein the combination of analytes present in the single sample includes N analytes, each of the N analytes configured to react with one of the N reagents, and wherein the presence of each of the N analytes reacting with its respective reagent is represented in the temporally varied signal as a step function where the signal level during the time interval during which each reagent optically changes is substantially constant and the signal level incrementally decreases at the start of each sequential time interval during which a reagent reacts with its respective analyte.

25. The multiple analyte detection system of claim 1, wherein the plurality of reagents includes N reagents, wherein the combination of analytes present in the single sample includes N−1 analytes, the single sample omitting one analyte corresponding to one of the N reagents such that the combination of analytes present in the single sample reacts with all but one of the N reagents, wherein the presence of each of the N−1 analytes reacting with its respective reagent is represented in the temporally varied signal as a step function where the signal level during the time interval during which each reagent optically changes is substantially constant, the signal level decreases at the start of each sequential time interval during which a reagent reacts with its respective analyte, and wherein there is no change in the signal level during the time interval in which the omitted analyte would have reacted with its respective reagent had the omitted analyte been present in the single sample.

26. The system of claim 17, wherein the single photodetector is stationary relative to the plurality of reagents during the measuring process.

* * * * *